US006753445B2

United States Patent
Ascher et al.

(10) Patent No.: US 6,753,445 B2
(45) Date of Patent: Jun. 22, 2004

(54) PLEUROMUTILIN DERIVATIVES HAVING ANTIBACTERIAL ACTIVITY

(75) Inventors: Gerd Ascher, Kundl (AT); Heinz Berner, Vienna (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 10/339,611

(22) Filed: Jan. 9, 2003

(65) Prior Publication Data

US 2003/0162831 A1 Aug. 28, 2003

Related U.S. Application Data

(63) Continuation-in-part of application No. PCT/EP01/07875, filed on Jul. 9, 2001.

(30) Foreign Application Priority Data

Jul. 11, 2000 (GB) .............................................. 0017031

(51) Int. Cl.[7] ........................ C07C 205/00; A01N 37/00
(52) U.S. Cl. ........................................ 560/125; 514/529
(58) Field of Search ........................... 560/125; 514/529

(56) References Cited

U.S. PATENT DOCUMENTS

| 4,675,330 A | 6/1987 | Berner et al. ................ 514/365 |
| 5,164,526 A | 11/1992 | Macher ........................ 560/16 |
| 6,130,250 A | 10/2000 | Burch et al. ................. 514/550 |

FOREIGN PATENT DOCUMENTS

| GB | 2121035 | 12/1983 |
| WO | WO 99/21855 | 5/1999 |
| WO | WO 00/27790 | 5/2000 |
| WO | WO 02/04414 | 1/2002 |

OTHER PUBLICATIONS

Egger and Reinshagen, J. *Antibiotics*, vol. XXIX, No. 9, pp. 915–927 (1976).

*Primary Examiner*—Paul J. Killos
(74) *Attorney, Agent, or Firm*—Diane E. Furman; John D. Thallemer

(57) ABSTRACT

A compound selected from 14—O—[(cycloalkyl-sulfanyl) acetyl]mutilins; 14—O—[(cycloalkyl-alkyl-sulfanyl)acetyl] mutilins; 14—O—[(cycloalkoxy)acetyl] mutilins; and 14—O—[(cycloalkyl-alkoxy)acetyl] mutilins and its use as a pharmaceutical.

9 Claims, No Drawings

PLEUROMUTILIN DERIVATIVES HAVING ANTIBACTERIAL ACTIVITY

This application is a continuation-in-part of PCT/EP01/07875 filed Jul. 9, 2001.

The present invention relates to antibacterials; more specifically to mutilins. Pleuromutilins are naturally occurring antibiotics which have antimycoplasmal activity and modest antibacterial activity. We have found mutilins having the principal ring structure of naturally occurring pleuromutilins which have improved antimicrobial, e.g. antibacterial activity.

In one aspect the present invention provides a compound selected from 14—O—[(cycloalkyl-sulfanyl)acetyl] mutilins; 14—O—[(cycloalkyl-alkyl-sulfanyl)acetyl] mutilins; 14—O—[(cycloalkoxy)acetyl] mutilins; and 14—O—[cycloalkyl-alkoxy)acetyl] mutilins; such as 14—O—[(aminocycloalkyl-sulfanyl)acetyl]mutilins; 14—O—[(aminocycloalkyl-alkyl-sulfanyl)acetyl] mutilins; 14—O—[(aminocycloalkoxy)acetyl] mutilins; and 14—O—[(aminocycloalkyl-alkoxy)acetyl] mutilins; preferably 14—O—[(aminocycloalkyl-sulfanyl)acetyl]mutilins; e.g. cycloalkyl is preferably $(C_{3-12})$cycloalkyl; cycloalkoxy is preferably $(C_{3-12})$cycloalkoxy; alkyl is preferably $(C_1)$alkyl; and alkoxy is preferably $(C_{1-4})$alkoxy.

In another aspect the present invention provides a compound of formula

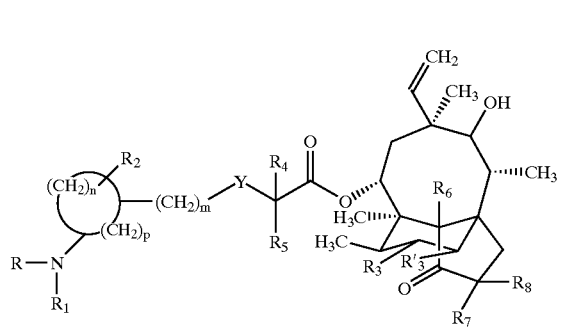

I wherein
R is hydrogen;
$R_1$ is hydrogen or a group of formula

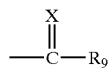

wherein
X is sulphur, oxygen or $NR_{10}$, wherein $R_{10}$, is hydrogen or alkyl; and
$R_9$ is amino, alkyl, aryl or heterocyclyl; and, if X is oxygen, $R_9$ is additionally hydrogen;
Y is sulphur or oxygen;
$R_2$ is hydrogen or one or more substituents, e.g. including substituents such as conventional in organic, e.g. (pleuro)mutilin, chemistry;
$R_4$ is hydrogen or alkyl;
$R_5$ is hydrogen or alkyl;
$R_3$ and $R_3'$ are hydrogen, deuterium, or halogen;
$R_6$, $R_7$ and $R_8$ are hydrogen or deuterium;
m is a number selected from 0 to 4;
n is a number selected from 0 to 10; and
p is a number selected from 0 to 10; with the proviso that n plus p are at least 1 and preferably less than 13.

In formula I, preferably
R is hydrogen;
$R_1$ is hydrogen or a group of the formula $-C(=X)R_9$, wherein X is oxygen; and
$R_9$, is alkyl, e.g. $(C_{1-8})$alkyl, such as $(C_{1-4})$alkyl, unsubstituted or substituted alkyl, e.g. substituted by groups which are conventional in organic, e.g. pleuromutilin, chemistry, such as one or more amino; e.g., if $R_9$ is alkyl substituted by amino, $R_9$ is preferably the residue of an amino acid, e.g. valine, e.g. said residue includes that part of an amino acid which remains if the carboxylic group is split off;
Y is sulphur;
$R_2$ is hydrogen;
$R_4$, $R_5$, $R_3$, $R'_3$, $R_6$, $R_7$, and $R_8$ are hydrogen;
m is o;
n is 3 or 4;
p is 0 or 1; and
p plus n is 3 or 4.

In another aspect, the invention provides a compound of the formula $I_p$

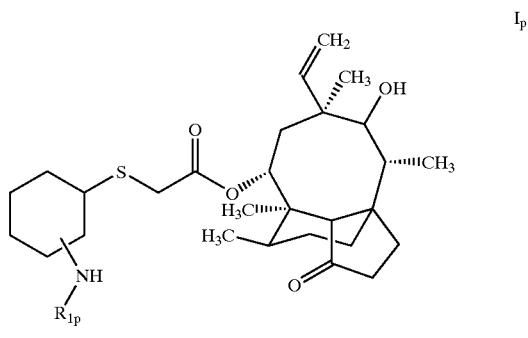

$I_p$ wherein $R_{1p}$ is hydrogen or the residue of an amino acid; e.g. valyl; e.g. $R_{1p}$ is a group of formula —CO—$R_{9p}$ wherein $R_{9p}$ is the residue of an amino acid which remains if the carboxylic group is split off.

In formula $I_p$ a group —NH—$R_{1p}$ may be in any position of the cyclohexyl ring system and is preferably in position 2, 3, or 4. Amino acid in the meaning of Rap includes any amino acid, preferably valine; and $R_{9p}$ is preferably a group —CH(NH$_2$)—CH(CH$_3$)$_2$. The amine group in said amino acid residue may be unprotected or protected, e.g. by appropriate amino acid protection groups, e.g. such as conventional, for example tert.butoxycarbonyl; and is preferably unprotected.

In another aspect, the present invention provides a compound which is:
14—O—[(aminocyclohexan-2-yl-sulfanyl)acetyl]mutilin,
14—O—[(aminocyclohexan-3-yl-sulfanyl)acetyl]mutilin,
14—O—[(aminocyclohexan-4-yl-sulfanyl)acetyl]mutilin,
14—O—[(N-valyl-aminocyclohexan-2-yl)sulfanyl)-acetyl]-mutilin,
14—O—[(N-valyl-aminocyclohexan-3-yl)sulfanyl)-acetyl]-mutilin, or
14—O—[(N-valyl-aminocyclohexan-4-yl)sulfanyl)-acetyl]-mutilin; including
14—O—[(N-(R)-valyl-(R)-aminocyclohexan-2(R)-yl)sulfanyl)-acetyl]-mutilin,
14—O—[(N-(R)-valyl-(R)-aminocyclohexan-2(S)-yl)sulfanyl)-acetyl]-mutilin,
14—O—[(N-(R)-valyl-(R)-aminocyclohexan-3(R)-yl)sulfanyl)-acetyl]-mutilin,
14—O—[(N-(R)-valyl-(R)-aminocyclohexan-3(S)-yl)sulfanyl)-acetyl]-mutilin;

14—O—[(N-(R)-valyl-cis-aminocyclohexan-4-yl)
sulfanyl)-acetyl]-mutilin, and
14—O—[(N-(R)-valyl-trans-aminocyclohexan-4-yl)
sulfanyl)-acetyl]-mutilin, e.g., in free (base) form or in the
form of a salt, such as a hydrochloride.

Preferred compounds include: 14—O—
[(aminocyclohexan-4-yl-sulfanyl)acetyl]mutilin and
14—O—[(N-valyl-aminocyclohexan-4-yl)sulfanyl)-
acetyl]-mutilin. More preferred is 14—O—[(N-valyl-
aminocyclohexan-4-yl)sulfanyl)-acetyl]-mutilin.

A compound provided by the present invention is here-
inafter designated as "A compound of the present inven-
tion". The present invention includes a compound of the
present invention, e.g. including a compound of formulae I
and $I_p$, in free (base) form and in the form of a salt, e.g. in
the form of a solvate.

In another aspect, the present invention provides a com-
pound of the present invention in the form of a salt, e.g. and
in the form of a salt and in the form of a solvate, or in the
form of a solvate.

A salt of a compound of the present invention includes a
pharmaceutically acceptable salt, e.g. including a metal salt
or an acid addition salt. Metal salts include for example
alkali or earth alkali salts; acid addition salts include salts of
a compound of the present invention with an acid, e.g.
hydrogen fumaric acid, fumaric acid, naphthalin-1,5-
sulfonic acid, hydrochloric acid, and deuterochloric acid;
preferably hydrochloric acid or deuterochloric acid.

A compound of the present invention in free form may be
converted into a corresponding compound in the form of a
salt; and vice versa. A compound of the present invention in
free form or in the form of a salt and in the form of a solvate
may be converted into a corresponding compound in free
form or in the form of a salt in unsolvated form; and vice
versa.

A compound of the present invention may exist in the
form of isomers and mixtures thereof; e.g. a compound of
the present invention may contain asymmetric carbon atoms
and may thus exist in the form of diastereoisomeres and
mixtures thereof. For example, in a compound of formula $I_p$,
wherein the group —NH—$R_{1p}$ is in position 2 or 3 of the
cyclohexyl ring, the carbon atom of the cyclohexyl ring
which is attached to the side chain of the mutilin ring and the
carbon atom of the cyclohexyl ring to which the group
—NH—$R_{1p}$ is attached are both asymmetric carbon atoms.
A compound of formula $I_p$ wherein the group —NH—$R_{1p}$ is
in position 2 or 3 of the cyclohexyl ring may thus exist in (R)
and (S) configurations in respect to both of these carbon
atoms. For example, if $R_{1p}$ is the residue of an amino acid,
that amino acid may comprise asymmetric carbon atoms.
E.g., if $R_{1p}$ is valyl, the carbon atom to which the amine
group of said valyl is attached is an asymmetric carbon
atom. A compound of formula $I_p$ wherein $R_{1p}$ is valyl may
thus exist in (R) and in (S) configurations in respect to said
valyl carbon atom.

Isomeric or diastereoisomeric mixtures may be separated
as appropriate, e.g. according to conventional methods, to
obtain pure isomers or diastereoismers, respectively. The
present invention includes a compound of the present inven-
tion in any isomeric and diasteroisomeric form and in any
isomeric and diastereoisomeric mixture. Preferably the con-
figuration in the mutilin ring of a compound of formula I is
the same as in a naturally produced pleuromutilin.

A compound of the present invention may be obtained as
appropriate, e.g. according to, e.g. analogously, to any
conventional method. E.g., 14-O-[(cycloalkyl-sulfanyl)
acetyl]mutilins; 14—O—[(cycloalkyl-alkyl-sulfanyl)acetyl]
mutilins; 14—O—[(cycloalkoxy)acetyl] mutilins; and
14—O—[(cycloalkyl-alkoxy)acetyl] mutilins of the present
invention may be prepared by reacting a 14—O—
[(mercapto)acetyl]mutilin or a 14—O—[(hydroxy)acetyl]
mutilin, respectively, with a hydroxycyclalkyl, or a
hydroxyalkyl-cycloalkyl, respectively, in an activated form,
e.g. in the form of an ester with a sulfonic acid, and isolating
a compound of the present invention from the reaction
mixture obtained.

Any compound of the present invention and any interme-
diate in the preparation of a compound of the present
invention may be obtained as appropriate, e.g. according,
such as analogously, to a conventional method, e.g. or as
specified herein, including the examples. A compound of
formula I or $I_p$ may be obtained. e.g. according. e.g.
analogously, to a process for the preparation of 14—O—
[(cycloalkyl-sulfanyl)acetyl]mutilins; 14—O—
[(cycloalkyl-alkyl-sulfanyl)acetyl] mutilins; 14—O—
[(cycloalkoxy)acetyl] mutilins; and14—O—[(cycloalkyl-
alkoxy)acetyl] mutilins.

In another aspect, the present invention provides a process
for the production of a compound of formula I comprising
the steps a. reacting a compound of formula II

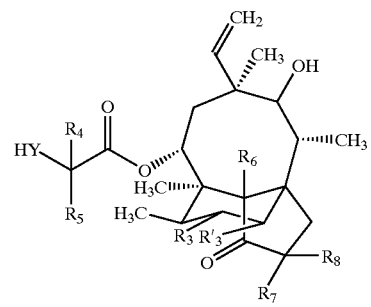

wherein Y, $R_3$, $R'_3$, $R_4$, and $R_5$ are as defined above and $R_6$,
$R_7$, and $R_8$ are hydrogen, with a compound of formula III

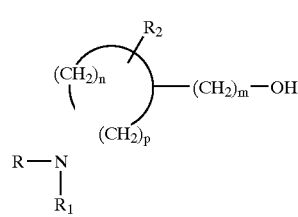

wherein R, $R_1$, $R_2$, m, n, and p are as defined above, in an
activated form, e.g. in the form of an ester with
4-toulenesulfonic acid (tosylate), or of an ester with meth-
ylsulfonic acid (mesylate), to obtain a compound of formula
I; wherein $R_6$, $R_7$ and $R_8$ are hydrogen and Y, $R_1$, R, $R_2$, $R_3$,
$R'_3$, $R_4$, $R_6$, m, n, and p are as defined above, and, if desired, b. introducing deuterium into a compound of formula I
obtained in step a, to obtain a compound of formula I,
wherein Y, $R_1$, R, $R_2$, $R_3$, $R'_3$, $R_4$, $R_5$, m, n, and p are as
defined above and $R_6$, $R_7$, and $R_8$ are deuterium.

A compound of formula II is known or may be obtained
according, e.g. analogously, to a conventional method. A
compound of formula III may be obtained as appropriate,
e.g. according, e.g. analogously, to a conventional process.
A compound of formula III may preferably be prepared
according to the following process, e.g. or as described in
the examples:

A dihydroxycycloalkyl or a (hydroxyalkyl)(hydroxy) cycloalkyl respectively, wherein $R_2$, m, p, and n are as defined above; may be reacted in solvent which is inert under the reaction conditions with 4-toluenesulfonic or methanesulfonic acid anhydride to obtain a corresponding di-tosyl/mesyl-oxycycloalkyl, or (tosyl/mesyl)oxyalkyl) (tosyl/mesyloxy) cycloalkyl respectively; which di-tosyl/ mesyl-compound is further reacted with sodium azide to obtain a corresponding (tosyl/mesyloxy)(azido)cycloalkyl, or a (tosyl/mesyloxyalkyl)(azido)cycloalkyl, respectively. In a (tosyl/mesyloxy)(azido)-compound obtained the azido group is reduced, e.g. catalytically hydrogenated, to obtain the corresponding (tosyl/mesyloxy)(amino)cycloalkyl, or (tosyl/mesyloxyalkyl)(amino)cycloalkyl, respectively; which is a compound of formula 111, wherein the hydroxy group is tosylated/mesylated; wherein R and $R_1$ are hydrogen and wherein $R_2$, m, p and, n are as defined above. If desired, the amine group obtained by reduction of the azido group may be reacted with $R_9$—C(=X)OH, wherein $R_9$ and X are as defined above, in an activated form, e.g. if X is oxygen R1—C(=X)OH may be in the form of an anhydride, halogenide; to obtain a compound of formula III, wherein R is hydrogen; $R_1$ is a group of formula —C(=X)R9, wherein X and $R_9$ are as defined above; and wherein $R_2$, m, p, and n are as defined above.

Replacement of hydrogen atoms in a compound of formula 1, e.g. in the form of a salt; by deuterium atoms may be carried out as appropriate, e.g. according, e.g. analogously, to a conventional method, e.g. or according to a method described herein; e.g. by treatment of a compound of formula 1, e.g. including a compound of formula Ip; with deuterochloric acid (DCI) in appropriate solvent (system) and isolation of a compound of formula I, e.g. in the form of a salt, wherein hydrogen atoms, e.g. in the meaning of $R_6$, $R_7$, and $R_8$ are replaced by deuterium atoms.

The production of a compound of formula I, wherein $R_3$ and $R'_3$ are deuterium or halogen may be carried out as appropriate, e.g. according, e.g. analogously, to a conventional method, e.g. via treatment of a compound of formula V

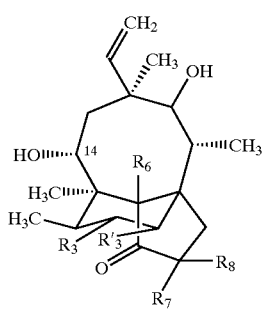

V wherein the carbon atoms carrying $R_3$ and $R'_3$, which both are hydrogen, together form a double bond and which is a known compound, with deuterium or with halogen, e.g. with $F_2$, $Cl_2$, or, $Br_2$, to obtain a compound of formula V, wherein $R_3$ and $R'_3$ are deuterium or halogen; and further reacting a compound of formula V, wherein $R_3$ and $R'_3$ are deuterium or halogen as appropriate, e.g. according, e.g. analogously, to a conventional method, to obtain a compound of formula II, wherein, $R_3$ and $R'_3$ are deuterium or halogen and $R_6$, $R_7$, and $R_8$ are hydrogen.

Preferably a compound of formula II may be obtained from a compound of formula V by reacting a compound of formula V with a compound of formula III

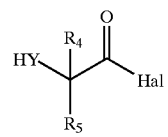

III wherein Y, $R_4$, and $R_5$ are as defined above and Hal is halogen, preferably bromo or chloro. A compound of formula III is known or may be obtained as appropriate, e.g. according, e.g. analogously, to a conventional method.

The compounds of the present invention, e.g. including a compound of formulae I and $I_p$, hereinafter designated as "active compound(s) of the present invention" exhibit pharmacological activity and are therefore useful as pharmaceuticals. For example, the active compounds of the present invention show antimicrobial, e.g. antibacterial, activity against gram positive bacteria, such as Staphylococci, e.g. *Staphylococcus aureus*, Streptococci, e.g. *Streptococcus pyogenes*, *Streptococcus pneumoniae*, Enterococci, e.g. *Enterococcus faecium*, as well as against mycoplasms, Chlamydia, and obligatory anaerobes, e.g. Bacteroides fragilis; in vitro in the Agar Dilution Test or Microdilution Test according to National Commitee for Clinical Laboratory Standards (NCCLS) 1997, Document M7-A4 Vol.17, No. 2: "Methods for dilution Antimicrobial Susceptibility Tests for Bacteria that Grow Aerobically—Fourth Edition, Approved Standard"; and in the Anaerobic Bacteria TEST according to National Committee for Clinical Laboratory Standards (NCCLS) VOL. 13, No. 26; M11-A4, Methods for Antimicrobal Susceptibility Testing of Anaerobic Bacteria; Approved Standard; Fourth Edition (1997). For example, the compound of example 1 shows in vitro in the above indicated Agar Dilution Test and/or Microdilution Test against bacterial strains as mentioned above MIC values of 0.01 to 1.0 µg/mL.

In another aspect, the present invention provides a compound of the present invention for use as a pharmaceutical, preferably as an antimicrobial, such as an antibiotic, e.g. and an anti-anaerobic.

In a further aspect, the present invention provides a compound of the present invention for use in the preparation of a medicament for the treatment of microbial diseases, for example of diseases caused by bacteria, e.g. selected from Staphylococci, Streptococci, Enterococci; e.g. and of diseases caused by mycoplasms, Chlamydia, and obligatory anaerobes.

In a further aspect, the present invention provides a method of treatment of microbial diseases which comprises administering to a subject in need of such treatment an effective amount of a compound of the present invention e.g. in the form of a pharmaceutical composition.

For antimicrobial treatment, the appropriate dosage will, of course, vary depending upon, for example, the active compound of the present invention employed, the host, the mode of administration, and the nature and severity of the conditions being treated. However, in general, for satisfactory results in larger mammals, for example humans, an indicated daily dosage is in the range from about 0.5 to 3 g, of an active compound of the present invention conveniently administered, for example, in divided doses up to four times a day.

An active compound of the present invention may be administered by any conventional route, preferably orally, e.g. in form of tablets, powders, capsules, or suspensions; e.g. including non-resorbable oral formulations; or parenterally, e.g. in the form of injectable solutions or suspensions; or topically, e.g. in the form of nasal sprays, body solutions, creams, or eye drops. The active compounds of the present invention may be administered in analogous manner, e.g. in similar doses and for similar indications, as erythromycin(s), tetracycline(s). Surprisingly the active compounds of the present invention show also activity against strains which are resistant against erythromycin(s), tetracycline(s).

The active compounds of the present invention may be administered in the form of a pharmaceutically acceptable salt, e.g. an acid addition salt or metal salt; or in free form; optionally in the form of a solvate. The active compounds of the present invention in the form of a salt exhibit the same order of activity as the active compounds of the present invention in free form. The active compounds of the present invention may be administered in the form of pharmaceutical compositions.

In another aspect he present invention provides a pharmaceutical composition comprising a compound of the present invention, e.g. in free form or in the form of a pharmaceutically acceptable salt; e.g. and/or in the form of a solvate; in association with at least one pharmaceutical carrier or diluent.

Such compositions may be manufactured according, e.g. analogously, to a conventional method. Unit dosage forms may contain, for e.g., about 100 mg to about 1 g.

The active compounds of the present invention are additionally suitable as veterinary agents, e.g. veterinary active compounds, e.g. in the prophylaxis and in the treatment of microbial, e.g. bacterial diseases, in animals, such as fowl, pigs, and calves; e.g. and for diluting fluids for artificial insemination and for egg-dipping techniques.

In another aspect, the present invention provides a compound of the present invention for use as a veterinary agent.

In a further aspect, the present invention provides a compound of the present invention for the preparation of a veterinary composition which is useful as a veterinary agent.

The present invention further provides a veterinary method for the prophylaxis and in the treatment of microbial, e.g. bacterial diseases, which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired. For example, for prophylactic treatment relatively low doses would be administered over a longer time period, e.g. 1 to 3 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff, and to calves orally or parenterally, e.g. in the form of oral or parenteral preparations.

In the following examples, which illustrate the invention, references to temperature are in degrees Celsius.

The following abbreviations are used:
DCCI dicyclohexylcarbodiimide
BOC tert.butoxycarbonyl
DMF dimethylformamide.

The numbering of the mutilin ring system referred to in the examples is given in the following formula:

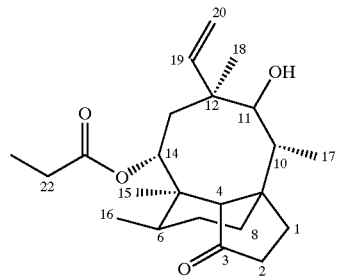

14—O—[(3-(R)-amino-2-methyl-propanecarbonylamino)-cyclohexane-1-yl)-sulfanyl)-acetyl]-mutilin (=14—O—[(N-(R)-valyl-(R)-aminocyclohexan-3(R)-yl)sulfanyl)-acetyl]-mutilin) A. 1,3-bis-(4-Toluene-sulfonyloxy)-cyclohexane A solution of 11.6 a of 1.3-dihydroxycyclohexane. 6.52 g of 4-toluenesulfonic acid anhydride and 40.4 g of N-methylmorpholine in 200 mL of methylenechloride is stirred for ca. 24 hours at room temperature. The reaction mixture obtained is poured onto 1 N HCl and the mixture obtained is extracted with methylenechloride. The organic phase obtained is dried and the solvent is evaporated off. 38.5 g of 1,3-bis-(4-toluene-sulfonyloxy)-cyclohexane are obtained. B. 1-Toluenesulfonyloxy-3-azido-cyclohexane To a solution of 3.9 of 1,3g-bis-(4-toluene-sulfonyloxy)-cyclohexane in 100 mL of DMF, 0.55 g of sodium azide is added in portions. The reaction mixture obtained is heated to ca. 80° for ca. 2 hours, the solvent is removed under vacuum, and the residue obtained is dissolved in 200 mL of methylene chloride and subjected to chromatography. 1.2 g of 1-toluenesulfonyloxy-3-azido-cyclohexane are obtained. $H^1$-NMR(CDCl$_3$): Mixture of diastereoisomeres: 7.8,7.3 (2xd, 4H, arom.H), 4.8,4.4(2xm,1H, CHO), 3.2,3.7(2xm, 1H,CHN), 2.4(s,3H,arom.CH$_3$),1.2–1.8(m,8H,cyclohexyl). C. 1-Toluenesulfonyloxy-3-(3(R)-tert.butyloxycarbonylamino-2-methyl-propanecarbonylamino)-cyclohexane A solution of 2.75 g of 1-toluenesulfonyloxy-3-azido-cyclohexane in 50 mL of ethyl acetate is hydrogenated in the presence of a catalytic amount of palladium on carbon (10%). The catalyst is filtrated off and 2.2 g of N-BOC-(D)-valine and 2 g of DCC are added to the filtrate obtained. The reaction mixture obtained is stirred for ca. 15 hours at room temperature, filtered and the solvent is evaporated off. The residue obtained is subjected to chromatography. 1.4 g of 1-toluenesulfonyloxy-3-(3(R)-tert. butyloxycarbonylamino-2-methyl-propanecarbonyl-amino)-cyclohexane are obtained. $H^1$-NMR(CDCl$_3$): Mixture of diastereoisomeres:7.8,7.3(2xm, 4H, arom.H), 6.5(m,1H, NH), 4.8,4,43(2xm, 1H,CHO), 3.85,3.55(2xm,1H, CHN), 3.62,3.7(2xm,1H,NCHCO), 2.4(s,3H,arom.CH$_3$),1.82(m, 1H,CHC(CH$_3$)$_2$), 1.38(b,9H,BOC), 0.78(m,6H, CHC(CH$_3$)$_2$).
D. 14-O-[(3-(3-(R)-Amino-2-methyl-propanecarbonylamino)-cyclohexane-1-yl)-sulfanyl-acetyl]-mutilin To a solution of 1.75 g of 14-mercaptoacetyl-mutilin and 70 mg of sodium in 100 mL of ethanol, 1.4 g of 1-toluenesulfonyloxy-3-(3(R)-tert.butyloxycarbonylamino-2-methyl-propanecarbonylamino)-cyclohexane and 0.7 mL of N-methylmorpholine are added. The mixture obtained is heated for ca 8 hours at ca. 90° C. The mixture obtained is poured onto brine, the mixture obtained is extracted with ethyl acetate, and the organic phase obtained is evaporated off. The residue obtained is treated with a mixture of trifluoroacetic acid/methylenechloride 1:1 and subjected to chromatography. 14-O-[(3-(3-(R)-amino-2-methyl-propanecarbonylamino)-cyclohexane-1-yl)-sulfanyl-acetyl]-mutilin is obtained. $H^1$-NMR($d_6$DMSO,350K): Mixture of diastereoisomeres:7.4(d,1 H,NH), 6.15(m,1 H,H19), 5.55(d,1H,H14), 5.05(m,2H,H20),4.5(d,1H,H11), 3.78(2xd,1H, NCHCO), 3.9(m,1H,NCH), 3.42(t,1H,H11), 3.25(m,2H,SCH$_2$CO),3.2(m,1HCHS), 0.9,0.88 (2xd,6H, (CH$_3$)$_2$CH), 1.08,1.36(2xs,6H,(CH$_3$)$_{18}$, (CH$_3$)$_{15}$), 0.65,0.83 (2xd,6H, (CH$_3$)$_{,6}$, (CH$_3$)$_{17}$). $^1$H-NMR (CDCl$_3$): ABX-system ($v_A$=3.15, $v_B$=3.22, $v_x$=1.92, 2H, H$_{22}$, J=15.8 Hz, J=8.2 Hz)

Example 2
A. N-(R)-(N-BOC-(R)-Valyl)-2(R)-hydroxy-cyclohexylamine

A mixture of 1.5 g trans-2-aminocyclohexanol, 2.17 g of BOC-(R)-valine, 2.06 g of DCC, and 1.01 g of N-methylmorpholine in 40 mL of CH$_2$Cl$_2$ is kept for ca. 24 hours at 250. A precipitate (urea) is formed and is filtrated off. The filtrate obtained is extracted with water, dried, the solvent is evaporated off, and the evaporation residue obtained is subjected to chromatograpy over silica gel. 710 mg of N-(R)-(N-BOC-(R)-valyl)-2(R)-hydroxy-cyclohexylamine are obtained. $H^1$ NMR (d$_6$DMSO, mixture of diastereoisomeres): 6.1,6.25(2xd,1H,CONH), 5.1,5.2 (2xb,1 H,BOC-HN), 3.85(m,1 H,a-H-val), 3.3,3.65(2xm, 2H,NCH,OCH).

B. N-(R)-(N-BOC-(R)-valyl)-2(R)-methansulfonyloxy-cyclohexylamine

A mixture of 710 mg of N-(R)-(N-BOC-(R)-valyl)-2(R)-hydroxy-cyclohexylamine, 393 mg of methanesulfonic acid anhydride, and 236 mg of N-methyl morpholine in 15 mL of CH$_2$Cl$_2$ is stirred at 250 for ca. 12 hours. The mixture obtained is extracted with 1N HCl, dried and the solvent is evaporated off. 685 mg of N-(R)-(N-BOC-(R)-valyl)-2(R)-methansulfonyloxy-cyclohexylamine are obtained.

C.14-O-[(N-(R)-Valyl-(R)-aminocyclohexan-2(S)-yl) sulfanyl)-acetyl]-mutilin in the form of a hydrochloride +(RSR)-Diastereomeres 1:1

A mixture of 588 mg of N-(R)-(N-BOC-(R)-valyl)-2(R)-methansulfonyloxy-cyclohexylamine, 591 mg of 22-desoxy-22-pleuromutilin-thiol, and 35 mg of sodium in 10 mL of dry ehthanol is stirred for ca. 24 hours at 25° and heated for ca. 2 hours at 90°. From the mixture obtained the solvent is evaporated off. To the evaporation residue ethyl acetate and water are added, the phases obtained are separated, and the organic phase is subjected to chromatography over silica gel. 14—O—[ (N-(R)-(N-BOC-(R)-valyl)-(R)-aminocyclohexan-2(S)-yl)sulfanyl)-acetyl]-mutilin is obtained and is treated with etheric HCl. 940 mg of 14—O—[ (N—R)—valyl—(R)-aminocyclohexan-2(S)-yl) sulfanyl)-acetyl]-mutilin-in the form of a hydrochloride are obtained. $H^1$NMR(d$_6$DMSO, 350K, mixture of diastereoisomeres): 6.15 (m,1H,H$_{19}$), 5.56, 5.58 (2xd, 1H,H$_{14}$), 5.1 (m,2H,H$_{20}$), 4.13(d,1H,OH, J=5.5 Hz), 3.43(t, 1H,H1,J=5.5 Hz), AB-system ($v_A$ =3.28,$v_B$=3.23, 2H,H22, J=14.7 Hz), 2.95(m,1H,CHS), 2.75(m,1H,CHNH), 0.65, 0.85 (2xd,6H, (CH$_3$)CH, 6.9 Hz), 1.08,1.37(2xs,6H,(CH$_3$) $_{18}$, (CH$_3$)$_{15}$.

D. 14-O-[ (N-(R)-Valyl-(R)-aminocyclohexan-2(R)-yl) sulfanyl)-acetyl]-mutilin in the form of a hydrochloride+ (RSR)-Diastereomeres 1:1

The title compound is obtained analogously as described in Example 2, step C), but using the appropriate starting materials, namely N-(R)-(N-BOC-(R)-valyl)-2(S)-methansulfonyloxy-cyclohexylamine instead of N-(R)-(N-BOC-(R)-valyl)-2(R)-methansulfonyloxy-cyclohexylamine. $H^1$NMR(d$_6$DMSO, 350K, mixture of diastereoisomeres): 8.0(b,3H,NH$_3$), 8.25(m, 1 H,NH), 6.15 (m,1H,H$_{19}$), 5.56, 5.58 (2xd, 1H,H$_{14}$), 5.1 (m,2H,H$_{20}$), 3.2–3.5(m, 5H,Hlll, NHCH, SCH,CH$_2$S), 3.6 (m,1H,α-H-val), 2.75(m,1H,CHNH), 0.65, 0.85 (2xd,6H, (CH$_3$)CH, 6.9 Hz), 1.08, 1.37(2xs,6H,(CH$_3$)$_{18}$, (CH$_3$)$_{15}$.

Example 3
14-0-[(N-valyl-aminocyclohexan-4-yl)sulfanyl)-acetyl]-mutilin in the form of a hydrochloride A. 14-O-[(Carbamimidoylsulfanyl)acetyl]mutilin-tosylate A solution of 15.2 g of thiourea and 106.4 g of pleuromutilin-22—O—tosylate in 250 mL of acetone is heated under reflux for 1.5 hours, solvent is removed under reduced pressure, and 100 mL of hexane is added. A precipitate forms, is filtrated off and dried. 14-O-[(carbamimidoylsulfanyl)acetyl]mutilin-tosylate is obtained. $^1$H-NMR (CDCl$_3$): AB-system ($v_A$=3.7, $v_B$ =3.82, 2H, H$_{22}$, J=15.8 Hz), 7.2 (d, 2H, arom.H, J=8 Hz), 7.75 (d, 2H, arom.H, J=8 Hz), 8.4, 9.8 (2xb, 4H, 2xNH$_2$).

B. 14-Mercapto-acetyl-mutilin

A solution of 4.7 g of sodium pyrosulfite (Na$_2$S$_2$O$_5$) in 25 mL of H$_2$O is added to a solution of 12.2 g of 14-O-[(carbamimidoylsulfanyl)acetyl]mutilin-tosylate in a mixture of 20 mL of ethanol and 35 mL of H$_2$O (warmed to ca. 900). 100 mL of CCl$_4$ are added to the reaction mixture obtained and the mixture is heated under reflux for ca. 2 hours. The two-phase system obtained is separated, the organic phase is dried, and the solvent is evaporated off. 14-Mercapto-acetyl-mutilin is obtained. $^1$H-NMR (CDCl$_3$): ABX-system ($v_A$=3.15, $v_B$=3.22, $v_x$=1.92, 2H, H$_{22}$, J=15.8 Hz, J=8.2 Hz).

C. 14-O-[(4-Amino-cyclohexyl-sulfanyl)acetyl]mutilin 394 mg of 14-mercapto-acetyl-mutilin are added under stirring at room temperature to a solution of 23 mg of sodium in absolute ethanol. The mixture obtained is treated with 190 mg of 4-(N-BOC-amino)cyclohexan-1-yl-p-tolueniesulfonate), prepared by reaction of 4-(N-BOC-amino)cyclohexanol with p-toluenesulfonic acid anhydride, and the mixture obtained is refluxed for ca. 2 hours. 14-O-[(N-BOC-aminocyclohexan-4-yl)sulfanyl)-acetyl]-mutilin is formed and is isolated from the reaction mixture and is treated with trifluoroacetic acid in order to split off BOC. 14-O-[(4-amino-cyclohexyl-sulfanyl)acetyl]mutilin is obtained. $^1$H-NMR (d6-DMSO): 7.9 (b,3H,NH$_3$), AB-system ($v_A$=3.23, $v_B$=3.29, 2H, H$_{22}$, J=15.2 Hz),3.03 (m,1H,SCH), 3.10(m,1H,CHN).

D. 14-0-[(N-valyl-aminocyclohexan-4-yl)sulfanyl)-acetyl]-mutilin in the form of a hydrochloride 60 mg of DCCI are added to a mixture of 65 mg of N-BOC-valin and 98 mg of 14-O-[(4-amino-cyclohexyl-sulfanyl)acetyl]mutilin in 10 mL of dichloromethane at room temperature and the mixture obtained is stirred for several hours at room temperature. A precipitate obtained is filtrated off and the filtrate obtained is concentrated under reduced pressure. The concentrate obtained is subjected to chromatography. 14-O-{{[N-(N-BOC-valyl)-aminocyclohexan-4-yl]sulfanyl}acetyl}-mutilin is obtained and is treated with etheric hydrochloric acid at room temperature for ca. 1 hour. From the mixture obtained the solvent is removed under reduced pressure and the residue obtained is precipitated. 14-O-[(N-valyl-aminocyclohexan-4-yl)sulfanyl)-acetyl]-mutilin in the form of a hydrochloride is obtained. $^1$H-NMR (d6-DMSO): 8.05 (b,3H,NH$_3$), 8.3(d, 1H,NH,J=6.7 Hz), AB-system ($v_A$=3.23, $v_B$=3.27,2H, H$_{22}$, J=15.2 Hz),2.98(m,1H,SCH), 3.75(m,1H,a-H, amino acid), 0.9(d,6H,2xCH3, J=5.9 Hz).

What is claimed is:

1. A compound which is a
   14—O—[(cycloalkyl-sulfanyl)acetyl]mutilin;
   14—O—[(cycloalkyl-alkyl-sulfanyl)acetyl] mutilin;
   14—O—[(cycloalkoxy)acetyl] mutilin; or
   14—O—[(cycloalkyl-alkoxy)acetyl] mutilin.

2. A compound of formula I

[Chemical structure of formula I]

wherein
R is hydrogen;
$R_1$ is hydrogen or a group of formula $$-\overset{X}{\underset{\|}{C}}-R_9$$

wherein
X is sulphur, oxygen, or $NR_{10}$, wherein $R_{10}$ is hydrogen or alkyl; and
$R_9$ is amino, alkyl, aryl, or heterocyclyl; and, if X is oxygen, $R_9$ is additionally hydrogen;
Y is sulphur or oxygen;
$R_2$ is hydrogen or one or more substituents;
$R_4$ is hydrogen or alkyl;
$R_5$ is hydrogen or alkyl;
$R_3$ and $R_3'$ are hydrogen, deuterium, or halogen;
$R_6$, $R_7$, and $R_8$ are hydrogen or deuterium;
m is a number selected from 0 to 4;
n is a number selected from 0 to 10; and
p is a number selected from 0 to 10; with the proviso that n plus p are at least 1.

3. A compound of the formula $I_p$

[Chemical structure of formula $I_p$]

wherein $R_{1P}$ is hydrogen or the residue of an amino acid.

4. A compound which is
   14—O—[(aminocyclohexan-2-yl-sulfanyl)acetyl] mutilin,
   14—O—[(aminocyclohexan-3-yl-sulfanyl)acetyl] mutilin,
   14—O—[(N-valyl-aminocyclohexan-2-yl)sulfanyl)-acetyl]-mutilin, or
   14—O—[(N-valyl-aminocyclohexan-3-yl)sulfanyl)-acetyl]-mutilin.

5. A compound which is
   14—O—[(aminocyclohexan-4-yl-sulfanyl)acetyl] mutilin, or
   14—O—[(N-valyl-aminocyclohexan-4-yl)sulfanyl)-acetyl]-mutilin.

6. A compound of claim 1 in the form of a salt.

7. A pharmaceutical composition comprising an effective amount of a compound of claim 1 and at least one pharmaceutical carrier or diluent therefor.

8. A method of treatment of microbial diseases which comprises administering to a subject in need of such treatment an effective amount of a compound of claim 1.

9. A method of claim 8 wherein the subject is a non-human animal.

* * * * *